US011229731B2

(12) United States Patent
Peters et al.

(10) Patent No.: US 11,229,731 B2
(45) Date of Patent: Jan. 25, 2022

(54) DISPLAY DEVICE FOR MEDICAL APPARATUS

(71) Applicant: B. BRAUN AVITUM AG, Melsungen (DE)

(72) Inventors: Meike Peters, Melsungen (DE); Sebastian Brögger, Knüllwald (DE); Björn Bröker, Staufenberg (DE); Bruno Stenzel, Münden (DE)

(73) Assignee: B. BRAUN AVITUM AG, Melsungen (DE)

( * ) Notice: Subject to any disclaimer, the term of this patent is extended or adjusted under 35 U.S.C. 154(b) by 610 days.

(21) Appl. No.: 15/644,164

(22) Filed: Jul. 7, 2017

(65) Prior Publication Data

US 2018/0015215 A1 Jan. 18, 2018

(30) Foreign Application Priority Data

Jul. 13, 2016 (DE) ..................... 10 2016 112 886.4

(51) Int. Cl.
*A61M 1/36* (2006.01)
*G06F 3/041* (2006.01)
(Continued)

(52) U.S. Cl.
CPC .............. *A61M 1/367* (2013.01); *A61M 1/14* (2013.01); *G03B 21/62* (2013.01); *G06F 3/0412* (2013.01);
(Continued)

(58) Field of Classification Search
CPC .......... A61B 5/742; A61B 5/743; A61M 1/14; A61M 1/367; A61M 2205/3306;
(Continued)

(56) References Cited

U.S. PATENT DOCUMENTS 6,629,927 B1 10/2003 Mesaros et al.
7,420,649 B2 9/2008 Duffield et al.
(Continued)

FOREIGN PATENT DOCUMENTS

CN 1839622 A 9/2006
CN 101430614 A 5/2009
(Continued)

OTHER PUBLICATIONS

DE102013111084A1 (EPO Machine Translation), 34 pages. (Year: 2019).*

(Continued)

*Primary Examiner* — Patrick Orme

(57) ABSTRACT

A display device for a medical apparatus including a projection surface arranged on the medical apparatus and configured to present a predetermined display content in a way visible to a user of the medical apparatus, and a projection device arranged on the medical apparatus and configured to project the predetermined display content from a rear side of the projection surface onto the projection surface. The projection surface and the projection device are configured as a head-up display unit for visual field presentation of the display content, and the medical apparatus may be an apparatus for carrying out extracorporeal blood treatment including the display device.

10 Claims, 1 Drawing Sheet

(51) Int. Cl.
*G16H 20/17* (2018.01)
*G16H 40/63* (2018.01)
*G03B 21/62* (2014.01)
*A61M 1/14* (2006.01)
*G06K 9/00* (2006.01)
*H04N 9/31* (2006.01)
*G03B 21/00* (2006.01)

(52) U.S. Cl.
CPC ......... *G06K 9/00335* (2013.01); *G16H 40/63* (2018.01); *H04N 9/3173* (2013.01); *A61M 2205/3306* (2013.01); *A61M 2205/505* (2013.01); *A61M 2205/584* (2013.01); *G03B 21/00* (2013.01); *G16H 20/17* (2018.01)

(58) Field of Classification Search
CPC ...... A61M 2205/505; A61M 2205/584; G03B 21/00; G03B 21/62; G06F 3/041; G06F 3/0412; G06F 19/3468; G06K 9/00335; G06K 9/00355; G16H 20/17; G16H 40/63; H04N 9/3173; H04N 13/0484; G02F 1/13338
See application file for complete search history.

(56) References Cited

U.S. PATENT DOCUMENTS

| | | | |
|---|---|---|---|
| 8,749,624 | B2 | 6/2014 | Marcus et al. |
| 9,330,525 | B2 | 5/2016 | Rasmussen et al. |
| 2008/0062115 | A1 | 3/2008 | Brown |
| 2009/0115744 | A1 | 5/2009 | Zhang et al. |
| 2012/0313775 | A1 | 12/2012 | Davis |
| 2014/0177909 | A1 | 6/2014 | Lin et al. |
| 2015/0070319 | A1* | 3/2015 | Pryor ................... G06F 3/0425 345/175 |
| 2015/0187196 | A1* | 7/2015 | Blair ..................... G16H 40/63 340/691.6 |
| 2015/0272694 | A1 | 10/2015 | Charles |
| 2016/0015330 | A1 | 1/2016 | Jo et al. |
| 2016/0132122 | A1 | 5/2016 | Steinle et al. |
| 2018/0015215 | A1 | 1/2018 | Peters et al. |

FOREIGN PATENT DOCUMENTS

| | | | | |
|---|---|---|---|---|
| CN | 102272656 | A | 12/2011 | |
| CN | 207424382 | U | 5/2018 | |
| DE | 102013111084 | A1 * | 4/2015 | ............. A61M 1/14 |
| DE | 102013111084 | A1 | 4/2015 | |
| EP | 1101502 | A2 * | 5/2001 | ......... A61M 1/3621 |
| EP | 1101502 | A2 | 5/2001 | |
| JP | 2004313324 | A * | 11/2004 | |
| JP | 2004313324 | A | 11/2004 | |
| WO | 2008030489 | A2 | 3/2008 | |
| WO | 2015153254 | A1 | 10/2015 | |
| WO | WO-2015153254 | A1 * | 10/2015 | ............. A61M 1/34 |

OTHER PUBLICATIONS

Extended European Search Report for European Application No. 17181266.2, dated Oct. 19, 2017 with translation, 17 pages. 2017.
German Search Report for German Application No. 10 2016 112 886.4, dated Mar. 10, 2017, with translation—17 Pages.
European Office Action for European Application No. 17 181 266.2, dated Jan. 22, 2019, with translation, 14 pages.
Chinese Office Action received in Application No. 201710566791.8 dated Oct. 9, 2020, 15 pages.
Office Action received in Japanese Application No. 2017-127736 dated May 18, 2021, with translation, 8 pages.

* cited by examiner

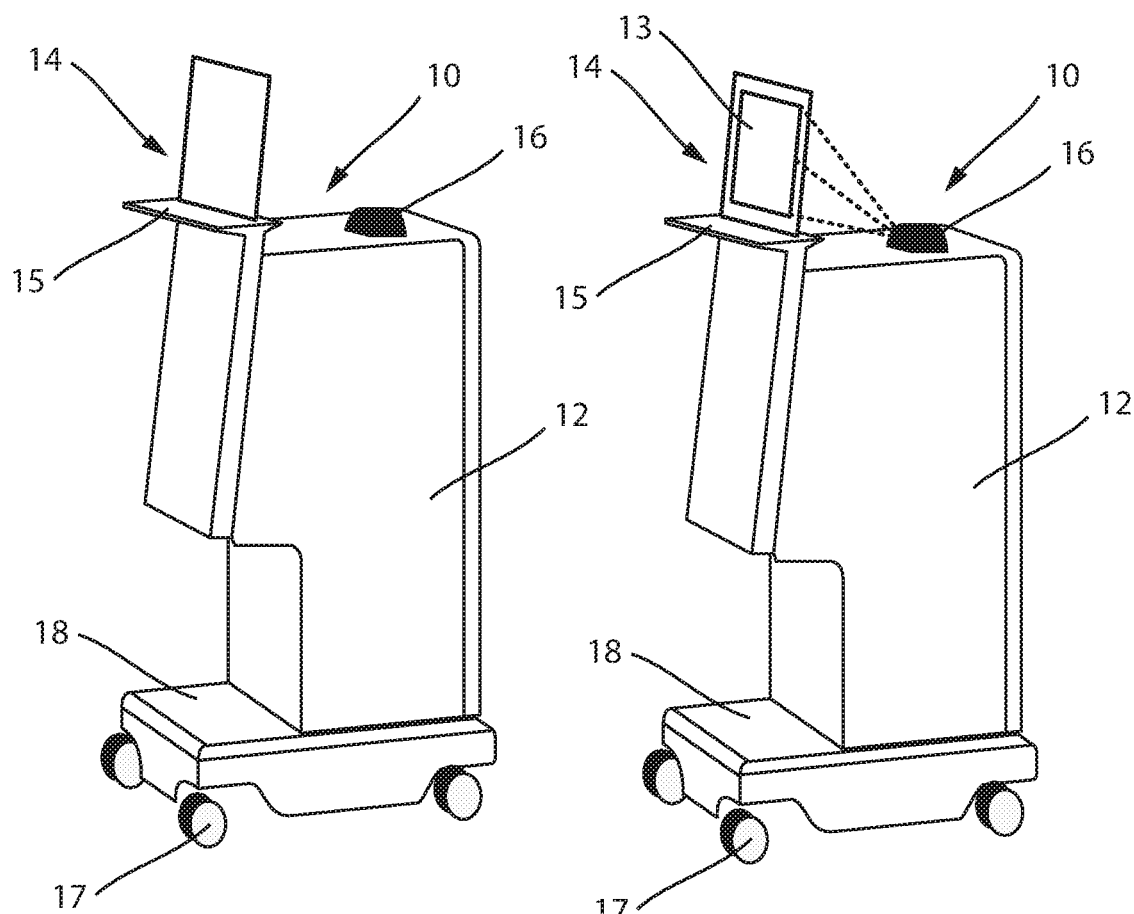
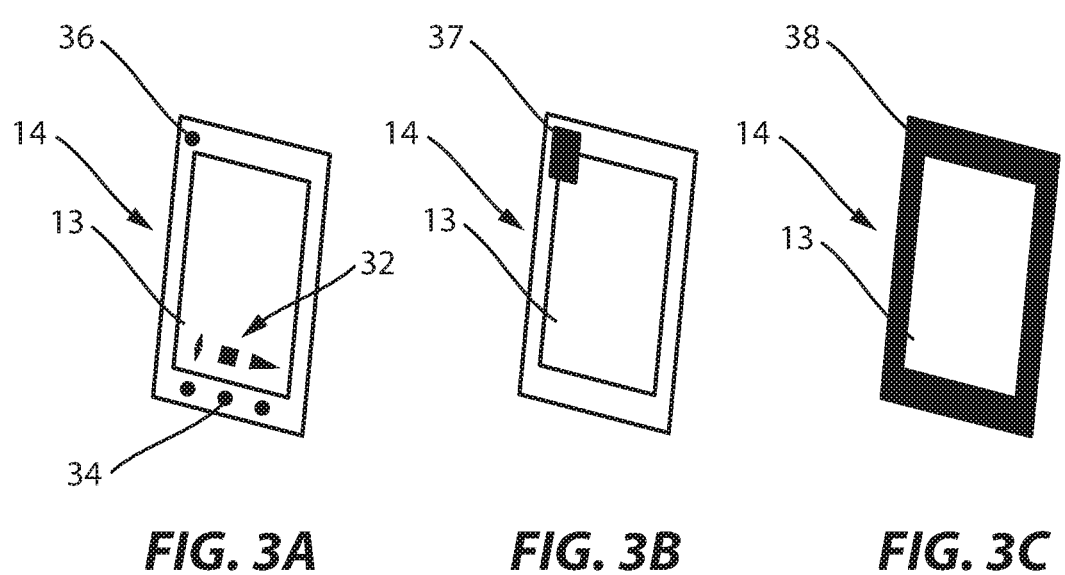

DISPLAY DEVICE FOR MEDICAL APPARATUS

CROSS REFERENCE TO RELATED APPLICATIONS

This application claims priority to German application DE 10 2016 112 886.4 filed Jul. 13, 2016, the contents of such application being incorporated by reference herein.

FIELD OF THE INVENTION

The invention relates to a display device for a medical apparatus, e.g. extracorporeal blood treatment machine/dialysis machine, and especially relates to a screen or monitor which is operable and/or adapted to present information according to the principle of a visual field presentation means or a HUD (Head Up Display).

BACKGROUND OF THE INVENTION

For example, in the field of the apparatuses for carrying out extracorporeal blood treatment, such as a dialysis machine, operating and display devices are usually configured as a monitor having an inherent housing or integrated in the apparatus housing. Due to the usually provided screen size, for example 38.1 cm corresponding to 15", complex measures for sealing and for sufficient EMC protection are required. Moreover, interfering contours impeding cleaning operations frequently form at a transition between the monitor housing and the screen. In addition, in systems comprising a touch-sensitive operating field, high requirements to the flatness of the housing in the area of the touch-sensitive surface have to be met. Additionally, parallax errors are frequently resulting by reason of the distance between the monitor and the touch-sensitive surface and the position of the operator or user relative to the front surface.

SUMMARY OF THE INVENTION

The object underlying aspects of the invention is to provide a display device for a medical apparatus which overcomes the afore-mentioned drawbacks and further ensures display of operating conditions, interactive operation and/or presentation of alarm indicators.

The general idea underlying the invention is to dispose in or at an apparatus for carrying out extracorporeal blood treatment a translucent projection surface that is illuminated by a projector. A preferred projecting direction is a direction in which no shadow of the operator or user is cast. The projection surface may be a glass pane, plastic material or any other material having appropriate opacity and may be freestanding and/or adjustable, for example tiltable, rotatable and/or height-adjustable. On the projection surface at least one interactive element may be provided which may be equipped with a capacitive or resistive sensor system (touch-sensitive layer or touchscreen). Interaction of the operator or user may be evaluated with a camera or any other optical or capacitive sensor system. For example, a configuration for 2D gesture detection/2D position detection on the projection plane, e.g. of a finger of the operator or user, and/or a configuration for 3D gesture detection may be implemented. Furthermore, on or at the projection surface operating elements such as key arrays or hard keys may be integrated. With the translucence of the projection surface an operating condition display of the medical apparatus is visible all around. In a case of alarm, the surface of the operating condition display may be configured to be larger than in other operating cases and may frame e.g. an information display area or illuminate the entire information display field and, respectively, the entire projection surface and/or superimpose an information display, wherein the signaling effect can be increased by reflections on the apparatus. A two-channel system of an interactive or input evaluation may be realized by evaluation with at least two position detection systems, for example a position detection system based on ultrasound and touch sensitivity and a position detection system based on a 3D camera system and infrared scanning with infrared barrier grid.

Along the afore-stated general idea, due to the freestanding projection surface both EMC susceptible electronics in the area of the display device (monitor) and EMC emissions are dropped, a dripping water resistance to be required e.g. under ingress protection IP21, can be more easily ensured, and due to the absence of a housing and consequently missing corners and/or edges cleaning is facilitated and resistance to disinfectants, for example, is increased. As the thin-film transistor displays provided in known arrangements are dropped, a projector adapted to have small dimensions can be employed and, accordingly, a display image size can be easily scaled as well as separate operating condition displays may be dropped. In total, moreover the manufacturing costs are lower and, in connection with a foldable projection surface or mounting thereof at the installation location by a technician, a packing volume of the apparatus is smaller, wherefrom in turn lower transport expenses are resulting.

In detail, the object is achieved by a display device of a medical apparatus comprising a projection surface that is arranged on the medical apparatus and is configured to present a predetermined display content in a way visible to a user of the medical apparatus and comprising a projection apparatus (light-emitting and spaced in parallel from the projection surface) which is arranged on the medical apparatus and is configured to project the predetermined display content from a rear side of the projection surface onto the projection surface.

Preferably, the projection surface is a translucent projection surface consisting of a material having an appropriate opacity and may consist of glass or plastic, for example. A projection surface made from glass advantageously has an improved scratch resistance and resistance to substances occurring in the environment of the apparatus (cleaning and disinfecting agents). A projection surface made from plastic advantageously provides increased breaking strength and may be designed to be more lightweight.

Preferably, the projection surface and/or the projection device is/are arranged on the medical apparatus/the housing thereof to be tiltable, rotatable and/or height-adjustable. If the projection device is made to be adjustable, it can be articulated/mounted to the medical apparatus/the housing thereof so that it can follow up an inclination, rotation and/or height adjustment of the projection surface in order to maintain projection of the predetermined display content.

Preferably, the display device further incorporates an interaction element arranged on the projection surface and being configured so as to detect interaction of the user in a touch-sensitive, for example capacitive or resistive, manner. Interaction detected in this way may be advantageously transmitted in a simple manner to a downstream control unit or signal processing unit for predetermined further processing.

Alternatively preferred, the display device further may comprise an imaging means and/or optical sensor means which is configured to detect interaction of the user in a contactless manner. Advantageously, such detection may occur via an integrated imaging system or camera system which is integrated in the projection device, for example, or is separately arranged.

Preferably, the display device is configured to carry out 2D and/or 3D gesture and/or position detection on a projection plane of the display device or the projection device. In this way, the operator or user to whom sort of a virtual user interface is presented with the projection can interact with the medical apparatus upon suitable approach to the virtual user interface, whereas no reaction of the medical apparatus is triggered at more remote positions.

Preferably, alternatively or additionally an operating element manually operable by the user may be integrated in the projection surface. Advantageously, the at least one operating element may be configured to be functionally hard-wired, i.e. a predetermined function may be permanently assigned thereto. Alternatively, advantageously, the at least one operating element may be functionally freely configurable, i.e. a predetermined function, for example out of a set of predetermined functions, may be assignable thereto via a device adjusting range or the like in a variable or temporary manner. The operating element may be an operating key, a turning actuator, a turning/pressing actuator or the like.

Preferably, in the display device a predetermined portion of the projection surface is provided for displaying of a predetermined operating condition of the medical apparatus.

Further preferred, in at least a first and a second operating condition a predetermined first and/or second portion of the projection surface may be controllably configured to display the first and second operating conditions in different colors, and in a third operating condition a predetermined third portion of the projection surface may be controllably configured to display the third operating condition in a color other than that of the first and second operating conditions, whereas the predetermined third portion is larger than the predetermined first portion and the predetermined second portion. Advantageously, in such configuration the predetermined first portion is a first partial area of the projection surface and the predetermined second portion is a second partial area of the projection surface, the first operating condition is a normal operating condition of the medical apparatus and the second operating condition is an indicating/notifying operating condition of the medical apparatus, and the predetermined third portion is a framing partial area or total area of the projection surface and the third operating condition is an alarm condition of the medical apparatus, wherein the display of the operating conditions may be superimposed to the display of the predetermined display content. Advantageously, as different colors for displaying respective different operating conditions traffic light colors green (for an ordinary or regular operating condition, for example), yellow (e.g. for an operating condition in which the medical apparatus outputs a message or the like and requires increased attention of the operator or user) and red (e.g. for an alarm operating condition such as when disruption or a critical situation occurs in the course of treatment) can be used. Further advantageously, the position and the size of the individual portions may be variable depending on an operating condition, a process status and/or an urgency, which renders the attention demanded from the operator or user controllable. For example, a portion illuminated in green may be provided to be purely confirmative in an unobtrusive size and at an unobtrusive position, a portion illuminated in yellow may be provided variable in size and/or position depending on urgency, and a portion illuminated in red which absolutely requires immediate measures may be provided to be superimposing in frame shape or over the full surface. Moreover, the luminosity and/or the frequency of the provision may be variable depending on parameters or depending on urgency.

Preferably, in the display device an at least two-channel input evaluation of an interaction by the user with at least a first and a second position detecting system is provided. Advantageously, the two-channel design of the evaluation required in some medical applications is made available in this way. Advantageously, the first position detecting system may include an ultrasonic means and a touch-sensitive means, and the second position detecting system may include a 3D camera and infrared scanning. The first and/or second position detecting system(s) can be integrated in the projection device, for example, or can be arranged elsewhere at a suited position with respect to the medical apparatus.

Preferably, in the display device the projection surface and the projection device are configured as a HUD unit (head-up display unit) for the visual field presentation of the display content.

Preferably, an apparatus for carrying out extracorporeal blood treatment as a medical apparatus comprises a display device in the afore-mentioned form and appropriate development.

BRIEF DESCRIPTION OF THE DRAWINGS

The invention is best understood from the following detailed description when read in connection with the accompanying drawings. Included in the drawings are the following figures:

FIG. 1 shows a schematic representation of a medical apparatus comprising a display device and a projection device according to an embodiment;

FIG. 2 shows a schematic representation of the medical apparatus according to FIG. 1 with activated projection of a display content onto a projection surface of the display device; and FIG. 3A shows a schematic representation of the projection surface comprising operating or interactive elements exemplified as keys or switches;

FIG. 3B shows a schematic representation of the projection surface comprising an operating condition display for normal or indicating operating condition of the medical apparatus; and FIG. 3C shows a schematic representation of the projection surface comprising an operating condition of the medical apparatus.

DETAILED DESCRIPTION OF THE PREFERRED EMBODIMENTS

As is shown in a simplified and schematic form in FIG. 1 and FIG. 2, a medical apparatus 10, for example a device for extracorporeal blood treatment such as a dialysis machine, comprises a housing 12 in or at which components required by the system are received on the inside and on the outside. The components required by the system of a respective actual medical apparatus 10 are known per se and in so far will neither be explicitly shown nor described in detail. The medical apparatus 10 may be arranged to be movable via rollers 17 on a base 18.

A projection surface 14 and a projector or projection device 16 arranged at a predetermined distance from the projection surface 14 in this embodiment form a display device for the medical apparatus 10 in which the projection surface 14 is arranged on the medical apparatus 10 and is configured so as to present a predetermined display content 13 in a way visible to a user of the medical apparatus 10, and the projection device 16 is equally arranged on the medical apparatus 10 and is configured so as to project the predetermined display content 13 from a rear side of the projection surface 14 onto the projection surface and, respectively, a projection plane located preferably on or at the projection surface 14.

The display device for the medical apparatus 10 comprising the projection surface 14 and the projection device 16 thus operates based on the principle of an information display means including a visual field presentation which is also referred to as head-up display (HUD).

More precisely, the display device in the present embodiment may include, for example, an information procurement unit and an image display control unit. The image display control unit may include a light source and a movable reflective element. The light source is arranged to emit a light beam. The display device and, respectively, the projection device 16 thereof are configured to project the light beam onto the projection surface 14, i.e. focused on a plane located in the projection surface 14, so as to display the display information. The information procurement unit may be coupled to one or more sensors and/or to a control unit and may collect measuring values or data detected by the one sensor or the plural sensors and/or parameters and/or information generated internally by the control unit, for example referring to a course of treatment or an apparatus condition, may process the collected data and/or the collected information according to a predetermined processing and may output the processed information in image form and/or text form, for example, without being limited thereto, to the image display control unit. The information procurement unit may further make available display control signals on the basis of the data for the image display control unit. The image display control unit may receive the processed information and project the latter onto the projection surface 14 and moreover may receive the display control signals to determine or adjust a position of the display information on the projection surface 14 with the movable reflective element, for instance.

In this embodiment, the projection surface 14 is a translucent projection surface made from a material having appropriate opacity, for example in the manner of a diffusion disc or the like. For example, the projection surface 14 may consist of glass or plastic material of predetermined size and thickness that is shaped in a planar manner and rigid, but at least warp resistant, into which the display information projection of the projection device 16 can be variable in size and fitted or irradiated onto a plane within the projection surface 14 so that the display content 13 is focused and presented to be legible for an operator or user.

Furthermore, in this embodiment the projection surface 14 and, where appropriate, also the projection device 16 are arranged to be tiltable, rotatable and/or height-adjustable.

For example, the projection surface 14 may be articulated to be swiveling with a hinge-type joint arrangement at a surface portion of the medical apparatus 10, e.g. at a table-shaped molding or elevation 15, such as to be foldable or tiltable in a direction forward and/or rearward relative to an end face of the medical apparatus 10, and/or to be rotatable about a height direction. An angle of rotation range and/or angle of inclination range may be provided, for example, within a range which, on the one hand, still enables readability of the display content 13 by a person standing in front of the medical apparatus 10 and, on the other hand, permits folding into a protective lying or idle position, e.g. into a softly sheathing recess at the table-shaped molding or elevation.

Furthermore, by way of example the projection surface 14 can be adjustable in its absolute height above ground e.g. by height adjustability of an arrangement articulating the projection surface 14 to the medical apparatus 10 at a predetermined inclined position in a direction upward and/or downward relative to an upper surface of the medical apparatus 10. Alternatively, for example the projection surface 14 can be guided within a frame arrangement and can be movable within the same, the frame arrangement being fixed at least in the height direction with respect to the medical apparatus 10. In a modification, the articulating device mentioned afore by way of example and/or a frame arrangement may be altogether configured to be movable in height such that the projection surface 14 can be immersed or inserted at least partially into a recess of the medical apparatus 10.

Electric conductor connections to be provided where necessary may be covered for this purpose in the articulating device and/or the frame arrangement and may be guided in appropriate overlength. In another modification, such electric conductor connections can be guided via a separable plug contact arrangement and the projection surface 14 can be formed to be removable as a whole so that in the case of break of the projection surface 14 easy replacement is possible and for example in a non-operating condition of the medical apparatus 10 the projection surface 14 can be stored at a place safely protecting the latter.

In this embodiment, furthermore an operating or interactive element 32 (see FIG. 3A) may be arranged on the projection surface 14 and may be configured to detect interaction of the user in a touch-sensitive, e.g. capacitive or resistive, manner. The interactive element 32 may be e.g. a software switch which is projected into the display content 13 by software control with the projection device 16 and the condition or actuation of which is detected via a preferably multi-point or multi-touch capable touch-sensitive layer on the projection surface 14 and which permits e.g. varying a parameter of the medical apparatus or makes control functions of the medical apparatus 10, such as start, stop and pausing of an operating cycle, recording of a time course and the like, accessible to the operator or user.

Alternatively or additionally, an imaging means and/or optical sensor means may be arranged which is configured for contactless detecting interaction of the user. In this case, a touch-sensitive layer may be omitted and interaction e.g. by a camera arrangement known per se as picture-taking and/or imaging means may detect the position of a finger of the operator or user and may guide the same for input evaluation to a downstream processing or control means, for example the microcontroller.

In this embodiment, it is possible with the afore-mentioned detecting means for detecting and evaluating interaction or input of an operator or user to perform 2D and/or 3D gesture and/or position detection on a projection plane of the projection device. In particular, an at least two-channel input evaluation of interaction of the user with at least first and second position detecting systems may be provided, wherein the first position detecting system may comprise e.g. an ultrasonic means and a touch-sensitive means and the second position detecting system may comprise, for example, a 3D camera and infrared scanning.

As a further alternative or in addition, at least one operating key 34 manually operable by the user can be integrated on the projection surface 14 and/or on the projection device 16 (see FIG. 3A). The at least one operating key 34 may be provided in the form of a hardware key (hard key), for example, which is configured to be functionally hard-wired, i.e. constantly triggers a predetermined function at the medical apparatus 10 or the projection device 16, for example, or in a comparable sense can be functionally freely configured, for example by program-dependent or operating cycle-dependent assignment by software in the manner of a function key.

Furthermore, in this embodiment a predetermined portion of the projection surface 14 is provided for display of a predetermined operating condition of the medical apparatus 10 which is configured, for example, to emphasize different operating conditions on the projection surface 14 in different colors and, in this way, to attract respective attention of the operator or user.

In a modification, for this purpose the projection device 16 may include an operating condition display portion (not shown) which may be adapted to form a second or secondary (sub)projection device, may be provided separately from or additionally to a display information projection portion in charge of the projection of the display information and, when controlled by e.g. a microcontroller, may be configured to display, to insert or to superimpose to the display information a preferably flat element in at least one area of the projection surface 14 clearly distinguishable by color from the display information, wherein light intensity, flash frequency (flashing light presentation), size, shape and/or position of the flat element can be variable depending on an associated operating condition and/or an urgency of the operating condition information to be transmitted thereby (see FIG. 3A to FIG. 3C).

For example, a configuration making use of so called traffic light colors may be such that a first operating condition display 36 which informs about trouble-free and regular operating condition (normal operating condition) is represented in green color, in a first size and/or shape and at a first position which may be a rather unobtrusive position within the projection surface, a second operating condition display 37 which informs about a second operating condition (indicating operating condition) or process during a treatment cycle which although being uncritical requires at least attention and/or possibly interaction by the operator or user is represented in yellow color, in a second size equal to or larger than the first size, and/or a second shape adapted to be distinguishable from the first shape and at a second position which may be a more noticeable position within the projection surface, and a third operating condition display 38 which informs about a third operating condition (alarm condition) or process during a treatment cycle which is critical and requires at least prompt interaction by the operator or user, is represented in red color, in a second size larger than the first and second sizes and/or a second shape adapted to be distinguishable from the first and second shapes and at a second position which may be a more noticeable position within the projection surface. In this embodiment, for example the first operating condition display 36 is represented by a round green point (FIG. 3A), the second operating condition display 37 is represented by a yellow rectangle larger than the round green point and the third operating condition display 38 is represented by a red frame surrounding the projection surface 14.

In other words, in this embodiment in at least the first and second operating conditions a predetermined first portion of the projection surface 14 is controllably configured to display the first and second operating conditions in different colors, and in a third operating condition a predetermined second portion of the projection surface 14 is controllably configured to display the third operating condition as compared to the first and second operating conditions in different color, the predetermined second portion preferably being larger than the predetermined first portion, wherein the predetermined first portion may be a first partial area of the projection surface 14, the first operating condition may be a normal operating condition of the medical apparatus 10 and the second operating condition may be an indicating operating condition of the medical apparatus 10, and the predetermined second portion may be a framing partial area or a total area of the projection surface 14 and the third operating condition may be an alarm condition of the medical apparatus 10, with the display of the operating conditions being adapted to be superimposed to the display of the predetermined display content 13.

In another modification of this embodiment, touch-sensitive interactive elements 32 (see FIG. 3A) may be combined with the first, second and/or third portions such that, for example, the operating condition display portion of the projection device or another control means of the medical apparatus 10 arranged for this purpose, when generating or carrying out an operating condition display, at the same time establishes a touch-sensitive interactive element 32 at an appropriate location on the projection surface 14 and activates the same for user input.

In this way, an operator or user may directly react to the operating condition display, for example reset an indicating or warning message (yellow) or trigger emergency stop in an alarm condition (red). In the latter case, it may be sufficient to touch any point within the (red) third portion of the third operating condition display for emergency stop or transition to a safe operating cycle of the medical apparatus 10, whereby, in this case a reaction time of an operator or user may be advantageously reduced.

As an alternative or in addition, particular gestures may be predefined which can be activated when outputting an associated operating condition display and upon activation are detected by the 2D and/or 3D position and/or gesture detection as a reaction of an operator or user to an operating condition that has occurred. In this case, for example a predetermined hand movement or position of two hands relative to each other in an alarm condition may trigger the emergency stop or the transition to the safe operating condition of the medical apparatus 10, whereas in a non-alarm condition the same hand movement or position of hands will not cause any reaction of the medical apparatus 10.

Hence, in total in this embodiment the projection surface 14 and the projection device 16 are thus configured, as afore-described, as a HUD unit for visual field presentation of display information (display content 13) to be projected onto the projection surface 14 and as such may form (passively and/or interactively) functional parts or components of a device for carrying out an extracorporeal blood treatment such as a dialysis machine.

As has been described in the foregoing, a display device for a medical apparatus 10 contains a projection surface 14 which is arranged on the medical apparatus 10 and is configured to present a predetermined display content 13 in a way visible to a user of the medical apparatus 10, and a projection device 16 which is arranged on the medical apparatus 10 and is configured to project the predetermined display content 13 from a rear side of the projection surface 14 onto the projection surface 14. The projection surface 14 and the projection device 16 are configured as HUD unit for the visual field presentation of the display content 13 and the medical apparatus 10 may be an apparatus for carrying out extracorporeal blood treatment comprising such display device.

In the foregoing, the invention has been described by way of a preferred embodiment. It is understood that details of the described preferred embodiment do not restrict the invention as such and in an obvious manner for those skilled in the art various changes, modifications and/or equivalents may result all of which as such come within the scope of protection of the invention defined by the enclosed claims.

The invention claimed is:

1. A display device of a medical apparatus, comprising:
a projection surface mounted to the medical apparatus and configured to present a predetermined display content to a user of the medical apparatus on a front side of the projection surface; and
a projection device mounted on the medical apparatus and configured to project the predetermined display content from a rear side of the projection surface onto the projection surface;
wherein a predetermined portion of the projection surface is provided for displaying at least one predetermined operating condition of the medical apparatus, and in at least a first and a second operating condition at least one of a predetermined first portion or a predetermined second portion of the projection surface is controllably configured to display the first and second operating conditions in different colors; and
wherein the display device further comprises at least one of:
at least one interactive element which is arranged on the projection surface and is configured to detect an interaction of the user in a touch-sensitive manner, or
at least one manually-operable key, actuator or switch integrated in the projection surface.

2. The display device according to claim 1, wherein the projection surface is a translucent projection surface made from semi-opaque material.

3. The display device according to claim 1, wherein at least the projection surface is arranged to be at least one of tiltable, rotatable or height-adjustable.

4. The display device according to claim 1, further comprising at least one of an imaging means or an optical sensor means configured to detect interaction of the user in a contactless manner.

5. The display device according to claim 1, wherein the display device is configured to carry out at least one of two-dimensional (2D) and/or three dimensional (3D) detection on a projection plane.

6. The display device according to claim 5, wherein the detection includes at least one of gesture detection or position detection.

7. The display device according to claim 1, wherein in the first operating condition the predetermined first portion of the projection surface is controllably configured to display the first operating condition, and in the second operating condition the predetermined second portion of the projection surface is controllably configured to display the second operating condition, and wherein in a third operating condition, a predetermined third portion of the projection surface is controllably configured to display the third operating condition in a color other than the colors of the first operating condition and the second operating condition, and wherein the predetermined third portion is larger than the predetermined first portion and the predetermined second portion.

8. The display device according to claim 1, wherein a first and a second position detecting system are provided for an at least two-channel input evaluation of the interaction of the user.

9. The display device according to claim 1, wherein the projection surface and the projection device are configured as a head-up display unit for visual field presentation of the display content.

10. An apparatus for carrying out extracorporeal blood treatment comprising a display device according to claim 1.

* * * * *